United States Patent [19]

Silver

[11] Patent Number: 4,787,098
[45] Date of Patent: Nov. 22, 1988

[54] METHOD FOR OBTAINING CALIBRATED TOMOGRAPHIC IMAGE DATA TO CORRECT FOR COLLIMATOR WIDTH DIFFERENCES

[75] Inventor: Michael D. Silver, Northbrook, Ill.

[73] Assignee: Kabushiki Kaisha Toshiba, Kawasaki, Japan

[21] Appl. No.: 37,149

[22] Filed: Apr. 10, 1987

[51] Int. Cl.⁴ .................. G01N 23/08; H05G 1/60
[52] U.S. Cl. ............................ 378/18; 378/4; 378/207; 378/904; 378/150
[58] Field of Search .............. 378/18, 19, 4, 207, 378/7, 901, 150

[56] References Cited

U.S. PATENT DOCUMENTS

| | | | |
|---|---|---|---|
| 4,298,799 | 11/1981 | Oliver | 378/7 |
| 4,497,061 | 1/1985 | Hounsfield | 378/18 |
| 4,672,650 | 6/1987 | Masanobu | 378/901 |

FOREIGN PATENT DOCUMENTS

| | | | |
|---|---|---|---|
| 2335854 | 7/1977 | France | 378/7 |
| 0121089 | 9/1979 | Japan | 378/18 |

Primary Examiner—Carolyn E. Fields
Assistant Examiner—Joseph A. Hynds
Attorney, Agent, or Firm—Finnegan, Henderson, Farabow, Garrett and Dunner

[57] ABSTRACT

A method for obtaining calibrated image data of a target object using a tomographic apparatus is provided. The calibrated image data is width-corrected to account for variations in the width of a collimator of the tomographic apparatus. The collimator is adjusted to one width setting when target object image data is obtained, and to another width setting when data for calibrating the target object image is obtained. The method of the present invention ensures that, notwithstanding the variation in collimator width, the target object image data is accurately calibrated.

5 Claims, 1 Drawing Sheet

METHOD FOR OBTAINING CALIBRATED TOMOGRAPHIC IMAGE DATA TO CORRECT FOR COLLIMATOR WIDTH DIFFERENCES

BACKGROUND OF THE INVENTION

I. Field of the Invention

This invention relates to a method for obtaining calibrated image data for a target object using a tomographic apparatus. The calibrated image data is corrected to compensate for the use of different collimator widths to obtain the calibrated image data. The calibrated image data, which have reduced systematic noise, are used to reconstruct a tomographic image of the target object.

II. Background Information

Conventional methods for obtaining image data for a target object with a tomographic apparatus include steps for calibrating the image data of the target object against image data obtained for a reference object. This calibration is performed in order to eliminate, from the image data for the target object, non-object-intrinsic information or inaccuracies which may be contained within the image data as a result of features of the tomographic apparatus and techniques utilized to obtain the image data using the tomographic apparatus.

Typically, a tomographic apparatus includes a radiation source for generating radiation beams, a collimator for collimating the radiation beams to restrict the beams to a slice, and a chamber through which these radiation beams are directed. The collimator typically has a plurality of blades for use in setting a width for the collimator. The chamber of the tomographic apparatus includes a portion specifically adapted for receipt of an object. The tomographic apparatus further includes a plurality of individual detectors located opposite the radiation source for detecting radiation emerging from the chamber at various points, a data aquisition unit and a memory for storing data.

Image data for the target object may be obtained by placing the target object within the portion of the chamber adapted for receipt of an object, setting the width of the collimator to a predetermined scan-of-interest width appropriate to the width of the portion or slice of the target object which is of interest, and subsequently subjecting the target object to radiation from the radiation source. The radiation from the radiation source will pass through the object and emerge from the chamber so as to be detected by the detectors positioned at various points opposite the radiation source. The intensity of each radiation beam emerging from the chamber will vary in accordance with the composition of the target object at the points through which each radiation beam has passed. Each detector responds to the emerging radiation detected at a given point by generating a response signal for the radiation detected at that point. The response signals are transferred to the data acquisition unit of the tomographic apparatus which generates image data for the target object. The image data are stored in the memory.

For various reasons, however, the composition of the target is not accurately reflected by the emerging radiation which is detected by the detectors when the target object is placed in the chamber portion and subjected to radiation, i.e., scanned. Accordingly, the image data generated when the target object is scanned is inaccurate and not ideal for reconstructing a tomographic image of the target object.

One reason why the image data obtained by scanning the target object is not ideal is that a portion of the radiation detected by a detector is scattered radiation. Most tomographic apparatus base the reconstruction of images on the detection of transmitted radiation only, and not also on scattered radiation. Transmitted radiation is attenuated as it traverses the target object according to composition and density of the target object, and emerges from the chamber at a position opposite the radiation source. Scattered radiation is deflected by the target object and emerges from the chamber at some position other than opposite the radiation source. Radiation may be deflected at more than one point within the target object. Accordingly, a detector may receive both transmitted radiation, which follows a straight path from the radiation source, and scattered radiation, which follows a single or multiply deflected path from the radiation source. The detectors are unable to distinguish between transmitted and scattered radiation. As a result, scattered radiation causes the generation of image data which is inaccurately indicative of target object composition and density. The typical target object scatters at least some measure of radiation. Anti-scattering devices may reduce, but not eliminate, the amount of scattered radiation that reaches the detectors.

Another reason for inaccurate image data may be that the radiation from the radiation source is polychromatic X-ray radiation comprising a continuum of energy levels. The generation of image data and reconstruction of tomographic images is based on the idealization of monochromatic radiation having a given discrete energy level. Typical tomographic apparatus include radiation sources which, however, emit polychromatic X-ray radiation, and which, therefore, produce inaccurate images from the image data obtained from a scan of the target object. Other reasons for inaccurate image data such as, for example, effects caused by radiation generated by non-point sources and differences between individual detectors may also exist.

To mitigate against the effects of scattering, polychromaticity, and other undesirable effects, as those effects appear in the image data obtained when scanning the target object, conventional methods for obtaining image data, as stated above, also scan a reference object, and calibrate the image data obtained for the target object against data obtained for the reference object. The reference object, which is chosen and scanned to obtain data for use in calibrating the data for the target object, typically has physical characteristics essentially similar to the target object in so far as the characteristics of the target object and reference object are related to undesirable effects caused by, for example, scattering and polychromaticity. The collimator of the tomographic apparatus is set to a predetermined reference object collimator width for the reference object scan.

The target object may be, for example, a human patient or a portion of a human patient, the patient being scanned in order to produce a tomographic image for diagnostic use. In such a case, the reference object selected for use in calibrating the image data for the target object is typically a cylinder of water. The water cylinder is chosen having an overall external size similar to the size of the patient, i.e., to the "field size" for the target object. The physical characteristics of water which relate to scattering and polychromaticity are substantially similar to those of the human patient. Both the human patient and the water cylinder demonstrate substantially similar responses to polychromatic X-ray radiation, and both scatter radiation in a similar manner.

Although the water cylinder is similar to the human patient in regard to overall external size, and to physical characteristics relating to, for example, scattering and polychromaticity, the water cylinder is distinct from the human patient in regard to external shape and the size and shape of internal organs. The water cylinder is devoid of internal components.

Accordingly, data obtained by scanning the water cylinder primarily capture undesirable effects such as scattering and polychromaticity, for an object of its size, but does not capture external shape and internal features. Data obtained by scanning the human patient capture the external and internal features of the patient and undesirable effects.

Since the data obtained by scanning the water cylinder and the data obtained by scanning the human patient differ only in that the data for the human patient scan capture external and internal physical features of the human patient (in addition to the undesirable effects also captured by the water cylinder data), the human patient data are differenced from the water cylinder scan data. This differencing eliminates, or at least minimizes, the scattering and polychromatic effects from the human patient data. The resulting difference data set, which is representative of a scan of the human patient, free of undesirable effects, is referred to as the calibrated image data set of the human patient.

The water cylinder used when obtaining calibrated image data for a human patient is typically of uniform dimensions (wall thickness and diameter) throughout. The data generated for the cylinder are adjusted to achieve a substantially flat or equivalent set of signal responses from the detectors, i.e., a flat profile. In order to achieve a flat profile, a compensation object, typically an aluminum wedge, which is concave where the water cylinder is convex, may be inserted in the tomographic apparatus chamber at a location between the radiation source and the portion of the chamber where the human patient would be placed.

Data obtained when the reference object, e.g., a water cylinder, is scanned and image data obtained when the target object, e.g., a human patient, is scanned are each processed to correct for detector-to-detector variations and variations of the radiation output by the source, and data obtained is processed to obtain logarithms of all data values. Specifically, a water cylinder-calibrated image data set is obtained by differencing the processed water cylinder data and processed patient scan data. The natural logarithms of this differenced data set are actually used to reconstruct a tomographic image of the patient. Notice that effects caused by the compensation object, i.e., aluminum wedge, mentioned in the previous paragraph cancel when the differencing operation is performed. The water cylinder data, the image data, and the water cylinder-calibrated image data all may be stored in the memory of the tomographic apparatus. The tomographic apparatus also comprises a data processing unit. The processing steps mentioned above are performed by the data processing unit.

The amount of radiation generated by the radiation source which reaches the chamber of the tomographic apparatus is proportional to the width of the collimator. Accordingly, the amount of radiation emerging from the chamber, and the response signals generated in response thereto are also proportional to the width of the collimator. The collimator width for the essentially featureless reference object, e.g., the water cylinder, is chosen to maximize the signal-to-noise ratio, where here noise refers to statistical (i.e. random) noise, in the scan data for the water cylinder. Water significantly attenuates radiation beams passing through the chamber of the tomographic apparatus. Such significant attenuation tends to make the signal-to-noise ratio low. Hence, to keep the signal-to-noise ratio as high as possible in the reconstructed tomographic images, the collimator width for the reference object scan is made as large as possible to allow the greatest flow of radiation through the chamber.

The same argument can be applied to the image data scan to suggest the widest possible collimator width for the target object, that is, human patient scan data. However, for human patient scans, other considerations are of greater importance than the consideration with respect to statistical noise. The maximum collimator width is not necessarily ideal for a slice of the human patient. The collimator width for the target object, i.e., the human patient, is preferably chosen to maximize diagnostic information and minimize patient irradiation. A narrow slice in the human patient, and correspondingly a small, possibly even the minimum, collimator width, may be necessary to image and localize a small internal structure, e.g., a tumor, in the human patient. On the other hand, given pertinent diagnostic considerations, a wide slice in the human patient, and correspondingly a wide, possibly even the maximum, collimator width, may be called for. Thus, the reasons for picking collimator slice widths for the reference object scan and the target object scan are not the same, and may therefore lead to a situation wherein different collimator slice widths are preferably chosen for the water cylinder and human patient scans.

As stated above, the reference object, i.e., water cylinder scan, was introduced to mitigate undesirable effects in the target object, i.e., human patient image data such as scattered radiation and polychromaticity, and ordinary processing, as mentioned previously, mitigates these undesirable effects even if the reference object and target object scans are performed using different collimator widths. However, if different collimator widths are used, a previously unmentioned undersirable effect may enter the reconstructed tomographic image.

As discussed above, the response signal generated by the detectors is proportional to the width of the collimator. But the width of the collimator may not be a constant width along the full length of the collimator. That is, the width of the collimator may fluctuate about its nominal width due to, for example, bowing of the blades that define the collimator or machining marks or nicks in these blades. And each collimator width setting has its own unique pattern of width fluctuation along the length of the collimator. Therefore, the signal response of the detectors may reflect this collimator width fluctuation. If different collimator widths are used for the reference scan and target scan, then the data sets of each scan reflect different collimator fluctuation patterns. These patterns do not cancel when forming the water cylinder-calibrated human patient data set by differencing. Hence, undesirable effects are in the water cylinder-calibrated patient image data and may appear in the reconstructed tomographic image.

In summary, a problem exists in that calibration of the image data for a human patient scan, obtained when the collimator has a given width, using data for a water cylinder scan, obtained when the collimator has another given width, minimizes scattering and polychromatic effects, yet use of the different collimator widths to obtain the data introduces other undesired effects in the reconstructed tomographic image.

SUMMARY OF THE INVENTION

Accordingly, an object of the present invention is to provide a method for obtaining calibrated image data of a target object, which accurately calibrates the image data against calibration data obtained by scanning a reference object to minimize undersirable effects such as, for example, X-ray scattering, polychromaticity, and off-focal radiation.

Another object of the present invention is to provide a method for obtaining calibrated image data having an improved signal-to-noise ratio, wherein the improvement is achieved by reducing noise in the calibrated data used to calibrate the image data of the target object.

Yet another object of the present invention is to provide a method for obtaining calibrated image data using collimator widths of varying size to scan slices of the target object having widths which vary in accordance with the collimator width.

Additional objects and advantages of the invention will be set forth in the description which follows, and in part, will be obvious from the description or may be learned by practice of the invention.

To achieve the foregoing objects, and in accordance with the purposes of the invention as embodied and broadly described herein, there is provided a method for obtaining calibrated image data of a target object with a tomographic apparatus having a radiation source for generating radiation beams, a collimator having a plurality of collimator width settings for collimating the radiation beams, a chamber through which the radiation beams are directed, the chamber having a portion adapted for receipt of an object, a plurality of detectors for detecting radiation emerging from the chamber and for generating response signals responsive to the detected radiation, a data acquisition unit for generating data representative of the response signals, a data processor and a memory, wherein the calibrated image data are used to reconstruct a tomographic image of the target object, said method comprising the steps of:

scanning a reference object having physical characteristics similar to the target object, wherein the step of scanning the reference object includes the substeps of: placing the reference object in the portion of the chamber; setting the width of the collimator to a predetermined reference object collimator width; directing radiation beams through the chamber; detecting radiation emerging from the chamber; generating reference object response signals thereto; and generating and storing reference object data for each of the detectors representative of the reference object response signals;

scanning the target object, wherein the step of scanning the target object includes the substeps of: placing the target object in the portion of the chamber; setting the width of the collimator to a predetermined target object collimator width; turning on the radiation source to direct radiation beams through the chamber; detecting radiation beams emerging from the chamber and generating target object response signals thereto; and generating and storing target object data for each of the detectors representative of the target object response signals;

obtaining processed width correction data for each of the detectors representative of a variation between response signals generated by each of the detectors for radiation directed through the chamber, the chamber being filled with a selected medium and the collimator being set at the predetermined reference object collimator width, and response signals generated by the detectors for radiation directed through the chamber, the chamber being filled with the said selected medium, and the collimator being set at the predetermined target object collimator width;

storing the processed width correction data for each of the detectors;

differencing the processed width correction data for each of the detectors from the reference object calibration data for each of the detectors to obtain width-corrected calibration data for each of the detectors; and differencing the target object data for each of the detectors from the width-corrected data for each of the detectors to obtain calibrated image data for use in reconstructing a tomographic image of the target object.

DESCRIPTION OF THE PREFERRED EMBODIMENT

Figures 1, 1A, 1B:
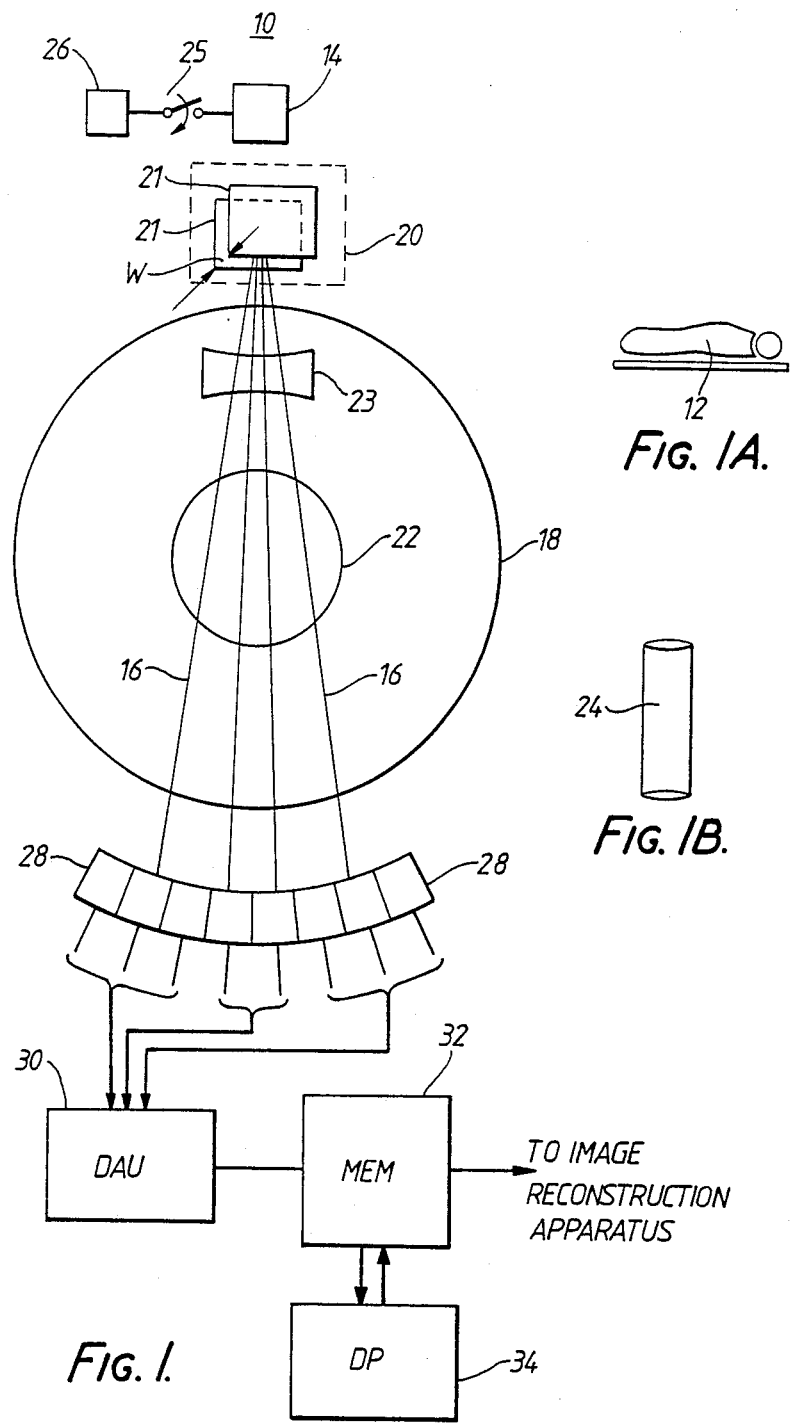
FIG. 1 illustrates a tomographic apparatus of the type which may be used in obtaining calibrated image data according to the method of the present invention.
FIGS. 1A and 1B depict a human patient and a water cylinder, respectively.

Referring to FIGS. 1, 1A and 1B a method for obtaining calibrated image data with a tomographic apparatus is described. The method is implemented using a tomographic apparatus, shown in FIG. 1, to obtain image data for a target object, shown in FIG. 1A. The image data is calibrated against data obtained for a reference object, shown in FIG. 1B.

As shown in FIG. 1, a tomographic apparatus 10, which may be used in obtaining calibrated image data for a target object such as, for example, a human patient 12 or a portion of a human patient 12 (shown in FIG. 1A), includes a radiation source 14 for generating radiation beams 16. Radiation beams 16 are directed through a chamber 18 which has a portion 22 specifically adapted for receipt of an object such as human patient 12 or a reference object which may be, for example, a water cylinder 24 (shown in FIG. 1B). Radiation source 14 may be of the type for emitting X-ray radiation which is polychromatic. Radiation source 14 may also be an extended radiation source of the type which emits off-focal radiation. A power source 26 is connected with radiation source 14 by means of a switch 25 in order to turn on radiation source 14 to direct radiation beams 16 through chamber 18.

A collimator 20 is interposed between radiation source 14 and portion 22 of chamber 18. Preferably, collimator 20 is interposed between radiation source 14 and chamber 18 as shown in FIG. 1. Collimator 20 collimates radiation beams 16 to direct the radiation beams in more nearly parallel form from radiation source 14 through chamber 18. Collimator 20 has a plurality of blades 21 which are used to adjust the width W of collimator 20, and to thereby also adjust the width of radiation beams 16 passing through chamber 18, i.e., the amount of radiation.

A plurality of individual detectors 28 are located opposite radiation source 14 and detect radiation emerging from chamber 18. Detectors 28 generate response signals in response to the radiation emerging from chamber 18.

An aluminum wedge 23 is removably positioned in chamber 18 between radiation source 14 and portion 22 of chamber 18. Aluminum wedge 23 is used to limit the dynamic range of the response signals generated by individual detectors 28. Specifically, aluminum wedge 23 attenuates radiation from radiation source 23 to compensate for the difference in path length for radiation beams passing through the center of an object positioned in portion 22 and for radiation beams passing through the periphery of such an object. Aluminum wedge 23 increases radiation beam path length for beams passing through the periphery of objects so that path lengths through objects for all beams are more nearly similar. The intensity of the radiation emerging from chamber 18 is, therefore, also made more similar for beams passing through the center and periphery of an object. The similarity in the intensity of radiation results in a limited dynamic range for the response signals and for greater precision in the response signals.

The response signals detected by individual detectors 28 are transferred to a data acquisition unit 30 which generates data representative of the received response signals. The representative data is subsequently transferred to a memory 32 which stores data, including data representative of response signals generated by detectors 28. The process of subjecting an object to radiation and generating representative data for storage in memory 32 is referred to as scanning. Data stored in memory 32 may be transferred to a data processor 34, processed and then transferred to memory 32 for storage.

The first step of the method of the present invention for obtaining calibrated image data involves the scanning of a reference object, such as a water cylinder 24 (FIG. 1B), to obtain reference object calibration data. The reference object calibration data, or, simply, calibration data, is used to eliminate undesirable effects such as scattering and polychromaticity from image data for a target object such as human patient 12.

Water cylinder 24, which has certain physical characteristics similar to those of human patient 12 (characteristics relating to scattering, polychromaticity, etc.) is placed in portion 22 of chamber 18. The width of collimator 20 is set to a predetermined reference object collimator width.

When the reference object is a water cylinder, the predetermined reference object scan width at which the collimator is set is, preferably, a maximum collimator width. By setting the collimator at the maximum width, the greatest amount of radiation is used to scan the reference object, water cylinder 24. Water cylinder 24 greatly attenuates the radiation passed therethrough, and accordingly may cause the generation of relatively noisy scan data. The relative proportion of noise in the scan data is preferably low, however. The proportion of noise may be made low by using a large amount of radiation to scan water cylinder 24. Using a large amount of radiation for the scan adds to the strength of signals used to generate the scan data without appreciably adding to the noise in the scan data.

Thereafter, radiation source 14 is turned on to direct radiation beams 16 through portion 22 of chamber 18. Radiation emerging from chamber 18 is detected by the plurality of individual detectors 28 located opposite radiation source 14. In response to the radiation detected by each individual detector 28, the individual detectors generate reference object response signals. The response signals are transferred to data acquisition unit (DAU) 30 which generates reference object calibration data representative of the reference object response signals. Preliminary processing of the data may be performed by data processor 34. Memory 32 stores the calibration data generated by DAU 30 and data processor 34.

Aluminum wedge 23 is positioned in chamber 18 when the scan of water cylinder 24 is performed. As described above, aluminum wedge 23 limits the dynamic range and improves the precision of the reference object response signals (and calibration data) obtained by performing the water cylinder scan.

Since water cylinder 24 demonstrates similar scattering and reactions to polychromaticity as human patient 24, but does not have the same shape or size as human patient 24, the calibration data can be used to eliminate undesirable effects from data obtained by scanning human patient 12, that is, to calibrate the human patient data. The calibration to eliminate undesirable effects is further described hereinafter. The visible manifestations of undesirable effects, which the calibration data is used to eliminate, or at least minimize, are commonly referred to as "artifacts." These visible manifestations appear in the reconstructed tomographic image of the human patient. "Dishing" and "ring" artifacts are among the known types of artifacts.

The calibration data generated from reference object response signals generated by detectors 28 is symbolized generally by the symbol $P_C$, where $P_C$ represents a profile or collection of reference object calibration data. Note that preliminary processing of the data corrects for detector-to-detector variations and variations of the radiation output by radiation source 14, and determines the natural logarithms of the data.

In performing the calibration of image data, an average calibration data profile $P_C$ (avg.) may be used in place of the profile $P_C$ obtained by performing a single reference object scan. An average profile may be obtained by performing several reference object scans and averaging the data therefrom. Average calibration data profiles $P_C$ (avg.) minimize any features of individual profiles unique to the individual profiles and not solely characteristic of the reference object, such as statistical, i.e., random noise.

The method of the present invention also includes a step whereby the target object, e.g., human patient 12, is scanned to obtain image data for the target object.

Human patient 12 is placed in portion 22 of chamber 18. The width of collimator 20 is set to a predetermined target object collimator width. The target object collimator width selected depends on the width of the portion or slice of human patient 12 which is of interest. For wide slices of human patient 12, the width of collimator 20 is set at a correspondingly large width, and possibly even at the maximum collimator width. But for a narrow slice of human patient 12, the collimator width is set at a correspondingly narrow width, and possibly even at a minimum collimator width. By setting the collimator width in accordance with the slice width, the radiation used to scan human patient 12 is limited to only that amount necessary to generate image data which captures the features of human patient 12 needed for diagnostic purposes.

Thereafter, radiation source 14 is turned on to direct radiation beams 16 through portion 22 of chamber 18. Radiation emerging from chamber 18 is detected by individual detectors 28 located opposite radiation source 14. In response to the radiation detected, individual detectors 28 generate target object response signals. The response signals are transferred to DAU 30 which generates image data representative of the target object response signals. This data may also be processed preliminarily by data processor 34. Memory 32 stores image data generated by DAU 30 and the data processor 34.

Aluminum wedge 23, which is positioned in chamber 18 for the reference object scan, is also positioned in chamber 18 for the target object scan. Positioning aluminum wedge 23 in chamber 18 for both the reference and target object scans maintains an essential similarity between the response signals and scan data generated for the scans. That is, a variation between data obtained when scanning water cylinder 24 and human patient 12, which is due to the presence or absence of aluminum wedge 23, is not introduced.

The target object image data captures features of human patient 12, such as size, shape and internal structure, and the effects of scattering and polychromaticity. Since the physical characteristics of human patient 12 and water cylinder 24 are similar in regard to scattering and polychromaticity, the undesirable effects captured by the target object scan data should be substantially similar to the effects as captured by the reference object calibration data. Thus, by calibrating the target object scan data against the reference object data, undesirable effects captured in the target object data are eliminated or minimized and calibrated image data obtained. This calibration is done in a subsequent step. However, in accordance with the teachings of the subject invention, before the calibration is performed, a width correction is performed on the calibration data to correct for any variation in reference object and target object response signals caused by the difference between the reference object collimator width used to obtain data when a reference object, such as water cylinder 24, is scanned and the target object collimator width used to obtain data when human patient 12 is scanned.

The target object image data obtained using target object response signals generated by detectors 28 is symbolized generally by the symbol $P_T$, where $P_T$ represents a profile or collection of target object image data. Preliminary processing of this data also corrects for detector-to-detector variations and variations of the radiation output by radiation source 14, and determines the natural logarithms of the data.

Once $P_C$ and $P_T$ have been obtained, the calibration data represented by $P_C$ is width-corrected for any variation between calibration data and target object image data caused by a difference between the predetermined maximum collimator width, preferably used to obtain calibration data or profile $P_C$, and the target object collimator width used to obtain the target object data or profile $P_T$. The target object image data $P_T$ is accurately calibrated by differencing the target object image data $P_T$ from the width-corrected calibration data. This differencing isolates the portion of the target object image data representative of the physical features of the target object, e.g., human patient 12, and eliminates the effects of scattering and polychromaticity. Calibrating the image data against calibration data which has not been width-corrected yields inaccurate calibrated image data which captures undetermined amounts of radiation representative of collimator width differences, and does not capture just the data representative of physical features of the target object.

Accordingly, in another step of the method of the present invention, a width correction profile, $P_W$, is obtained. Width correction profile $P_W$ captures the differences in response signals generated by detectors 28 for scans taken at the target object collimator width and at the reference object collimator width. $P_W$ is differenced from $P_C$ to obtain a width-corrected calibration profile $P_{WC}$.

$$P_{WC} = P_C - P_W \tag{1}$$

The substeps set forth below are used to obtain $P_W$. The width of collimator 20 is set at the maximum collimator width used when water cylinder 24 is scanned. Chamber 18, including portion 22 is preferably emptied to contain only air. That is, aluminum wedge 23 is removed and neither the water cylinder 24, human patient 12, nor any other object is placed in the chamber. Radiation source 14 is turned on to direct radiation beams 16 through chamber 18. Radiation emerging from chamber 18 is detected by individual detectors 28. First width correction response signals are generated by the detectors, and transferred to DAU 30 which generates a first set of width correction data, that is, a profile representative of the width correction response signals. The first width correction profile is stored in memory 32. The profile is here represented by the symbol $P_F$. Profile $P_F$ is also processed preliminarily by data processor 34 to correct for detector and source variations, and to obtain natural logarithms.

The substeps used to obtain $P_W$ further include the following substeps. The width of collimator 20 is set to the collimator width used to obtain target object profile $P_T$. Chamber 18 is kept empty. Radiation source 14 is turned on to direct radiation beams 16 through chamber 18. Radiation emerging from chamber 18 is detected by individual detectors 28. Second width correction response signals are generated by the detectors and transferred to DAU 30 which generates a second set of width correction data, that is, a profile representative of the second width correction response signals. The second width correction profile is stored in memory 32. The profile is here represented by the symbol $P_S$. Profile $P_S$ is also processed preliminarily.

After $P_F$ and $P_S$ have been obtained, the profiles are transferred to data processor 34, and $P_S$ is differenced from $P_F$. The difference obtained is the width correction profile $P_W$ which is used to width correct the calibration profile $P_C$.

$$P_W = P_F - P_S \tag{2}$$

Since the procedure used to obtain $P_F$ and $P_S$ is identical except for the width of the collimator, the scan data or profiles for the scans vary only as a function of collimator width. By differencing data for the scans, the amount of the variation due to collimator width difference is obtained. This difference $P_W$ is stored in memory 32 and subsequently differenced from $P_C$ to ensure that the elimination of undesirable effects captured in $P_T$ using $P_C$ is not prevented. (See equation (1).) As described above, that elimination is not possible if the profiles $P_T$ and $P_C$ vary due, in unknown part, to collimator width differences.

Differencing of $P_W$ and $P_C$ is performed by data processor 34. The difference, that is, the width-corrected calibration profile $P_{WC}$ is stored in memory 32.

In a final step, target object profile $P_T$ is differenced from width-corrected calibration profile $P_{WC}$ to obtain width-corrected calibrated image data for use in reconstructing a tomographic image of the target object, human patient 12. Where the width-corrected, calibrated target object image data, i.e., profile is represented by $\overline{P}$, $\overline{P}$ is given by the following equation:

$$\overline{P} = P_{WC} - P_T \tag{3}$$

The width-corrected, calibrated image data has low noise, is obtained using the lowest possible amount of radiation to scan human patient 12, and minimizes inaccuracies due to undesirable effects such as scattering and polychromaticity.

A profile for the calibrated image data used to reconstruct a tomographic image of human patient 12, $\overline{P}$ may be given in terms of all other profiles described:

$$\overline{P} = [P_C - (P_F - P_S)] - P_T \tag{4}$$

In actuality, in performing the above-described method, width correction scans need not be performed each time it is desired to obtain calibrated image data of a human patient. Rather, profiles $P_W$ (see equation (2)) may be obtained a first time, stored and updated infrequently, as when collimator 20 or radiation source 14 is replaced or serviced.

A separate profile $P_W$ is needed for each different combination of the maximum width and a smaller width, that is, for each variation between the maximum collimator width and some other width which may be used to scan human patient 12. It will be noted that no width correction profile $P_W$ is needed when the maximum collimator width is also used to scan human patient 12. In such a case there is no collimator width difference. Accordingly, with collimator width constant there should be no difference in scan data attributable to collimator width variation.

$P_C$ profiles also need not be performed each time it is desired to obtain calibrated image data of human patient 12. Scans to obtain $P_C$ may be performed infrequently, as for example, once a day or once a week. The profiles are stored in memory 32 for use at times in between times when the scans to obtain $P_C$ are actually performed.

$P_F$ and $P_S$ profiles, which are used to obtain $P_W$, may be performed several times. Averaged results of $P_F$ and $P_S$ may be differenced to obtain $P_W$. An average $P_W$ profile contains less noise than a $P_W$ profile obtained from single $P_F$ and $P_S$ profiles.

Tomographic apparatus of the type considered here may have the capacity to obtain profiles using any one of a plurality of resolution modes. The method of the present invention achieves its desired results as long as all profiles necessary for the implementation of the method are obtained using the same resolution mode.

The method described above is generally applicable for all tomographic apparatus as described in connection with FIG. 1. Included among the tomographic apparatus for which the method of the present invention is applicable are so called "third" and "fourth" generation CT-scanners. The radiation source and detectors for a third generation CT-scanner rotate about an object as the object is scanned. The source and detectors maintained fixed positions relative to one another. Detectors for fourth generation scanners remain stationary as the radiation source rotates about an object located in the chamber and about the detectors. Regardless of the position of the source and detectors when the scans are performed, the objects of the invention may be achieved using either of these types of scanners.

It should be apparent to those skilled in the art that various modifications and variations may be made to the method for obtaining calibrated image data of the present invention without departing from the scope or spirit of the invention. Thus, it is intended that the invention cover modifications and variations of the invention, provided they come within the scope of the appended claims including legally entitled equivalents.

I claim:

1. A method for obtaining calibrated image data of a target object with a tomographic apparatus having a radiation source for generating radiation beams, a collimator having a plurality of collimator width settings for collimating the radiation beams, a chamber through which the radiation beams are directed, the chamber having a portion adapted for receipt of an object, a plurality of detectors for detecting radiation emerging from the chamber and for generating response signals responsive to the detected radiation, a data acquisition unit for generating data representative of the response signals, a data processor and a memory, wherein the calibrated image data are used to reconstruct a tomographic image of the target object, said method comprising the steps of:

scanning a reference object having physical characteristics similar to the target object, wherein the step of scanning the reference object includes the substeps of: placing the reference object in the portion of the chamber; setting the width of the collimator to a predetermined reference object collimator width; directing radiation beams through the chamber; detecting radiation emerging from the chamber; generating reference object response signals thereto; and generating and storing reference object data for each of the detectors representative of the reference object response signals;

scanning the target object, wherein the step of scanning the target object includes the substeps of: placing the target object in the portion of the chamber; setting the width of the collimator to a predetermined target object collimator width; turning on the radiation source to direct radiation beams through the chamber; detecting radiation beams emerging from the chamber and generating target object response signals thereto; and generating and storing target object data for each of the detectors representative of the target object response signals;

obtaining processed width correction data for each of the detectors representative of a variation between response signals generated by each of the detectors for radiation directed through the chamber, with the chamber having a selected medium through which said radiation is directed and the collimator being set at the predetermined reference object collimator width, and response signals generated by the detectors for radiation directed through the chamber with the chamber having said selected medium, and the collimator being set at the predetermined target object collimator width;

storing the processed width correction data for each of the detectors;

differencing the processed width correction data for each of the detectors from the reference object calibration data for each of the detectors to obtain width-corrected calibration data for each of the detectors; and differencing the target object data for each of the detectors from the width-corrected data for each of the detectors to obtain calibrated image data for use in reconstructing a tomographic image of the target object.

2. The method according to claim 1, wherein the step of obtaining the processed width correction data for each of the detectors includes the substeps of:

setting the width of the collimator to the predetermined reference object collimator width; turning on the radiation source to direct radiation beams through the chamber when the portion of the chamber contains only air; detecting radiation beams emerging from the chamber; generating first width correction response signals thereto; generating and storing first width correction data for each of the detectors representative of the first width correction response signals;

setting the width of the collimator to the predetermined target object collimator width; turning on the radiation source to direct radiation beams through the chamber when the portion of the chamber contains only air; detecting radiation beams emerging from the chamber; generating second width correction response signals thereto; generating and storing second width correction data for each of the detectors represenative of the second width correction response signals; and differencing the second width correction data for each of the detectors from the first width correction data for each of the detectors to obtain the processed width correction data.

3. The method according to claim 2, wherein the plurality of collimator width settings includes a maximum width collimator setting, and wherein the predetermined reference object collimator width is the same as the maximum collimator width.

4. The method according to claim 2, wherein the method further includes the step of:

placing an aluminum wedge, for limiting the dynamic range of the reference object and target object response signals, between the radiation source and the portion of the chamber before radiation is directed through the chamber to permit detection of the reference object and target object response signals.

5. The method according to claim 4, wherein the method further includes the step of removing the aluminum wedge before the processed width correction data for each of the detectors is determined.

* * * * *